(12) United States Patent
    Chernova

(10) Patent No.: US 9,909,125 B2
(45) Date of Patent: Mar. 6, 2018

(54) MOLECULAR TARGETS FOR SELECTIVE ERADICATION OF SENESCENT CELLS

(71) Applicant: Everon Biosciences, Inc., Buffalo, NY (US)

(72) Inventor: Olga Chernova, Orchard Park, NY (US)

(73) Assignee: EVERON BIOSCIENCES, INC., Buffalo, NY (US)

( * ) Notice: Subject to any disclaimer, the term of this patent is extended or adjusted under 35 U.S.C. 154(b) by 0 days.

(21) Appl. No.: 15/032,954

(22) PCT Filed: Oct. 31, 2014

(86) PCT No.: PCT/US2014/063371
§ 371 (c)(1),
(2) Date: Apr. 28, 2016

(87) PCT Pub. No.: WO2015/066442
PCT Pub. Date: May 7, 2015

(65) Prior Publication Data
US 2016/0281085 A1    Sep. 29, 2016

Related U.S. Application Data

(60) Provisional application No. 61/898,904, filed on Nov. 1, 2013.

(51) Int. Cl.
    *C12N 15/113*    (2010.01)
(52) U.S. Cl.
    CPC ........ *C12N 15/113* (2013.01); *C12N 2310/14* (2013.01); *C12N 2310/531* (2013.01); *C12N 2320/31* (2013.01)
(58) Field of Classification Search
    None
    See application file for complete search history.

(56) References Cited

U.S. PATENT DOCUMENTS

2013/0288980 A1    10/2013    De Keizer et al.

FOREIGN PATENT DOCUMENTS

WO    WO 9711170 A1 *    3/1997    ......... C12N 15/1136
WO    2013/090645 A1    6/2013

OTHER PUBLICATIONS

Collado, M., et al, Tumour biology: senescence in premalignant tumours, Nature, Aug. 4, 2005, vol. 436, No. 7051, p. 642.
Kortlever, R.M., et al., Plasminogen activator inhibitor-1 is a critical downstream target of p53 in the induction of replicative senescence, Aug. 2006, Nat. Cell Biol., vol. 8, No. 8, pp. 877-884.
Collado, M., et al., Senescence in tumours: evidence from mice and humans, Jan. 2010, Nat. Rev. Cancer, vol. 10, No. 1, pp. 51-57.
Kumar, L.D., et al., Gene manipulation through the use of small interfering RNA (siRNA): from in vitro to in vivo applications, Mar. 30, 2007, Adv. Drug Deliv. Rev., vol. 59, pp. 87-100.
Vandekerckhove, L., et al., Transient and stable knockdown of the integrase cofactor LEDGF/p75 reveals its role in the replication cycle of human immunodeficiency virus, Feb. 2006, J. Virol., vol. 80, No. 4, pp. 1886-1896.

* cited by examiner

*Primary Examiner* — Tracy Vivlemore
(74) *Attorney, Agent, or Firm* — Hodgson Russ LLP

(57) ABSTRACT

Compositions and methods for selective partial or complete eradication of senescent cells in a mammal are provided. The involves inhibition of the expression of genes that are identified as being related to a senescent phenotype. The inhibition is produced using methods which include but are not necessarily limited to pharmacological inhibition, or inhibition by using RNAi-mediated approaches. As a consequence of selectively targeting senescent cells, prolonging or restoring healthy physiological conditions in a mammal can be achieved, and age related conditions can be treated or prevented, and undesirable accumulated senescent cells can be reduced or eradicated from a variety of tissues.

19 Claims, 4 Drawing Sheets

SEQUENCE LISTING

```
<160> NUMBER OF SEQ ID NOS: 47

<210> SEQ ID NO 1
<211> LENGTH: 57
<212> TYPE: DNA
<213> ORGANISM: artificial sequence
<220> FEATURE:
<223> OTHER INFORMATION: shRNA

<400> SEQUENCE: 1
gccaacaaag tcatcatgta agttaatatt catagcttac gtgatgactt tgttggc      57

<210> SEQ ID NO 2
<211> LENGTH: 57
<212> TYPE: DNA
<213> ORGANISM: artificial sequence
<220> FEATURE:
<223> OTHER INFORMATION: shRNA coding sequence

<400> SEQUENCE: 2
gcatccaacc atgtttatca agttaatatt catagcttga tgaacatggt tggatgc      57

<210> SEQ ID NO 3
<211> LENGTH: 57
<212> TYPE: DNA
<213> ORGANISM: artificial sequence
<220> FEATURE:
<223> OTHER INFORMATION: shRNA coding sequence

<400> SEQUENCE: 3
ctgggtgggg atgaatagga tgttaatatt catagcatcc tgttcatcct cacccag      57

<210> SEQ ID NO 4
<211> LENGTH: 57
<212> TYPE: DNA
<213> ORGANISM: artificial sequence
<220> FEATURE:
<223> OTHER INFORMATION: shRNA

<400> SEQUENCE: 4
gctcattctt cagttggaaa tgttaatatt catagcattt ccgactgaag agtgagc      57
```

```
<210> SEQ ID NO 5
<211> LENGTH: 57
<212> TYPE: DNA
<213> ORGANISM: artificial sequence
<220> FEATURE:
<223> OTHER INFORMATION: ShRNA coding sequence

<400> SEQUENCE: 5
cactgggagt aaataaggga agttaatatt catagcttcc cttgtttgct cccagtg      57

<210> SEQ ID NO 6
<211> LENGTH: 57
<212> TYPE: DNA
<213> ORGANISM: artificial sequence
<220> FEATURE:
<223> OTHER INFORMATION: ShRNA coding sequence

<400> SEQUENCE: 6
gcctgattca agtgtttatc agttaatatt catagctgat agacacttga atcaggc      57

<210> SEQ ID NO 7
<211> LENGTH: 57
<212> TYPE: DNA
<213> ORGANISM: artificial sequence
<220> FEATURE:
<223> OTHER INFORMATION: ShRNA coding sequence

<400> SEQUENCE: 7
cctgatatcc tacacaataa agttaatatt catagctttg ttgtgtagga tatcagg      57

<210> SEQ ID NO 8
<211> LENGTH: 57
<212> TYPE: DNA
<213> ORGANISM: artificial sequence
<220> FEATURE:
<223> OTHER INFORMATION: ShRNA coding sequence

<400> SEQUENCE: 8
tggacacttt acagactttg tgttaatatt catagcgcaa agtctgtaaa gtgtcca      57

<210> SEQ ID NO 9
<211> LENGTH: 57
<212> TYPE: DNA
<213> ORGANISM: artificial sequence
<220> FEATURE:
<223> OTHER INFORMATION: ShRNA coding sequence

<400> SEQUENCE: 9
gcctttggtg ttcaagctat agttaatatt catagctatg gcttggagac caaaggc      57

<210> SEQ ID NO 10
<211> LENGTH: 57
<212> TYPE: DNA
<213> ORGANISM: artificial sequence
<220> FEATURE:
<223> OTHER INFORMATION: ShRNA coding sequence

<400> SEQUENCE: 10
cccacatcct cactaagatt tgttaatatt catagcgaat cttggtgagg atgtggg      57

<210> SEQ ID NO 11
<211> LENGTH: 57
<212> TYPE: DNA
<213> ORGANISM: artificial sequence
<220> FEATURE:
<223> OTHER INFORMATION: ShRNA coding sequence
```

<400> SEQUENCE: 11
cgtgaaagtc ataaggatga agttaatatt catagcttca tccttgtgac tttcacg    57

<210> SEQ ID NO 12
<211> LENGTH: 57
<212> TYPE: DNA
<213> ORGANISM: artificial sequence
<220> FEATURE:
<223> OTHER INFORMATION: ShRNA coding sequence

<400> SEQUENCE: 12
gctaaatatg tctaaggaga tgttaatatt catagcatct ccttggacat atttagc    57

<210> SEQ ID NO 13
<211> LENGTH: 57
<212> TYPE: DNA
<213> ORGANISM: artificial sequence
<220> FEATURE:
<223> OTHER INFORMATION: ShRNA coding sequence

<400> SEQUENCE: 13
ctggacaact ttgtacttaa tgttaatatt catagcatta ggtacaaagt tgtccag    57

<210> SEQ ID NO 14
<211> LENGTH: 57
<212> TYPE: DNA
<213> ORGANISM: artificial sequence
<220> FEATURE:
<223> OTHER INFORMATION: ShRNA coding sequence

<400> SEQUENCE: 14
cctgataaca agtaaggata tgttaatatt catagcatat ccttgcttgt tatcagg    57

<210> SEQ ID NO 15
<211> LENGTH: 57
<212> TYPE: DNA
<213> ORGANISM: artificial sequence
<220> FEATURE:
<223> OTHER INFORMATION: ShRNA coding sequence

<400> SEQUENCE: 15
cagactggtg atgtagtttg tgttaatatt catagcacaa gctacatcgc cagtctg    57

<210> SEQ ID NO 16
<211> LENGTH: 56
<212> TYPE: DNA
<213> ORGANISM: artificial sequence
<220> FEATURE:
<223> OTHER INFORMATION: ShRNA coding sequence

<400> SEQUENCE: 16
ataacggtgc taactctata tgttaatatt catagcatat agagttagca ccgtta    56

<210> SEQ ID NO 17
<211> LENGTH: 57
<212> TYPE: DNA
<213> ORGANISM: artificial sequence
<220> FEATURE:
<223> OTHER INFORMATION: ShRNA coding sequence

<400> SEQUENCE: 17
gctgagttgg tggatgttct tgttaatatt catagcaaga gcatccacca gctcagc    57

<210> SEQ ID NO 18
<211> LENGTH: 57

```
<212> TYPE: DNA
<213> ORGANISM: artificial sequence
<220> FEATURE:
<223> OTHER INFORMATION: ShRNA coding sequence

<400> SEQUENCE: 18
gcacgacttc taggcattga agttaatatt catagcttca gtgcctggaa gtcgtgc       57

<210> SEQ ID NO 19
<211> LENGTH: 57
<212> TYPE: DNA
<213> ORGANISM: artificial sequence
<220> FEATURE:
<223> OTHER INFORMATION: ShRNA coding sequence

<400> SEQUENCE: 19
ctctgttgta tatccttcat tgttaatatt catagcaatg aaggatatac aacagag       57

<210> SEQ ID NO 20
<211> LENGTH: 57
<212> TYPE: DNA
<213> ORGANISM: artificial sequence
<220> FEATURE:
<223> OTHER INFORMATION: ShRNA coding sequence

<400> SEQUENCE: 20
gcaggaatcg tgtgattaat agttaatatt catagctatt agtcacacga ttcctgc       57

<210> SEQ ID NO 21
<211> LENGTH: 57
<212> TYPE: DNA
<213> ORGANISM: artificial sequence
<220> FEATURE:
<223> OTHER INFORMATION: ShRNA coding sequence

<400> SEQUENCE: 21
gatcaatttg actacaggat tgttaatatt catagcaatc ctgtagtcaa attgatc       57

<210> SEQ ID NO 22
<211> LENGTH: 57
<212> TYPE: DNA
<213> ORGANISM: artificial sequence
<220> FEATURE:
<223> OTHER INFORMATION: ShRNA coding sequence

<400> SEQUENCE: 22
gctggtggtt taagggttgg agttaatatt catagcttca acctttaaac caccagc       57

<210> SEQ ID NO 23
<211> LENGTH: 57
<212> TYPE: DNA
<213> ORGANISM: artificial sequence
<220> FEATURE:
<223> OTHER INFORMATION: ShRNA coding sequence

<400> SEQUENCE: 23
ccaccagctt ctttgaggtt tgttaatatt catagcaagc ctcagagaag ctggtgg       57

<210> SEQ ID NO 24
<211> LENGTH: 57
<212> TYPE: DNA
<213> ORGANISM: artificial sequence
<220> FEATURE:
<223> OTHER INFORMATION: ShRNA coding sequence

<400> SEQUENCE: 24
```
gtgtggttga aactagtat ggttaatatt catagccata ctggttctca gccacac    57

<210> SEQ ID NO 25
<211> LENGTH: 57
<212> TYPE: DNA
<213> ORGANISM: artificial sequence
<220> FEATURE:
<223> OTHER INFORMATION: ShRNA coding sequence

<400> SEQUENCE: 25
gtgtgagaat agctaagagt tgttaatatt catagcaact cttggctatt ctcacac    57

<210> SEQ ID NO 26
<211> LENGTH: 57
<212> TYPE: DNA
<213> ORGANISM: artificial sequence
<220> FEATURE:
<223> OTHER INFORMATION: ShRNA coding sequence

<400> SEQUENCE: 26
gcctcagtga tatagtataa agttaatatt catagcttta tactgtatca ctgaggc    57

<210> SEQ ID NO 27
<211> LENGTH: 57
<212> TYPE: DNA
<213> ORGANISM: artificial sequence
<220> FEATURE:
<223> OTHER INFORMATION: ShRNA coding sequence

<400> SEQUENCE: 27
gcagttgaag aaacatacaa tgttaatatt catagcattg tatgtttctt caactgc    57

<210> SEQ ID NO 28
<211> LENGTH: 57
<212> TYPE: DNA
<213> ORGANISM: artificial sequence
<220> FEATURE:
<223> OTHER INFORMATION: ShRNA coding sequence

<400> SEQUENCE: 28
cgtggtggag attgctaaag tgttaatatt catagcactt tggcaatttc caccacg    57

<210> SEQ ID NO 29
<211> LENGTH: 57
<212> TYPE: DNA
<213> ORGANISM: artificial sequence
<220> FEATURE:
<223> OTHER INFORMATION: ShRNA coding sequence

<400> SEQUENCE: 29
gcaagttgga atgatgttga agttaatatt catagcttca acatcattcc agcttgc    57

<210> SEQ ID NO 30
<211> LENGTH: 57
<212> TYPE: DNA
<213> ORGANISM: artificial sequence
<220> FEATURE:
<223> OTHER INFORMATION: ShRNA coding sequence

<400> SEQUENCE: 30
cctctcaatc aagatattca agttaatatt catagcttga gtatcttgat tgagagg    57

<210> SEQ ID NO 31
<211> LENGTH: 57
<212> TYPE: DNA
<213> ORGANISM: artificial sequence
<220> FEATURE:
<223> OTHER INFORMATION: ShRNA coding sequence

<400> SEQUENCE: 31
ctggtttctg gaggaaagag ggttaatatt catagctctc tttcctccag aagccag      57

<210> SEQ ID NO 32
<211> LENGTH: 57
<212> TYPE: DNA
<213> ORGANISM: artificial sequence
<220> FEATURE:
<223> OTHER INFORMATION: ShRNA coding sequence

<400> SEQUENCE: 32
gaagcgtagc agtatattaa agttaatatt catagctttg atatactgct acgcttc      57

<210> SEQ ID NO 33
<211> LENGTH: 57
<212> TYPE: DNA
<213> ORGANISM: artificial sequence
<220> FEATURE:
<223> OTHER INFORMATION: SH RNA coding sequence

<400> SEQUENCE: 33
cacctaccta gtgactatga tgttaatatt catagcatca tggtcactgg gtaggtg      57

<210> SEQ ID NO 34
<211> LENGTH: 57
<212> TYPE: DNA
<213> ORGANISM: artificial sequence
<220> FEATURE:
<223> OTHER INFORMATION: ShRNA coding sequence

<400> SEQUENCE: 34
gcatggatct ttgtactaag agttaatatt catagctctt ggtacgaaga tccatgc      57

<210> SEQ ID NO 35
<211> LENGTH: 57
<212> TYPE: DNA
<213> ORGANISM: artificial sequence
<220> FEATURE:
<223> OTHER INFORMATION: ShRNA coding sequence

<400> SEQUENCE: 35
ccaggaagat actggatgta ggttaatatt catagcttac atccggtatc ttcctgg      57

<210> SEQ ID NO 36
<211> LENGTH: 57
<212> TYPE: DNA
<213> ORGANISM: artificial sequence
<220> FEATURE:
<223> OTHER INFORMATION: ShRNA coding sequence

<400> SEQUENCE: 36
tcattcacta aggaaggaat tgttaatatt catagcaatt ccttccttag tgaatga      57

<210> SEQ ID NO 37
<211> LENGTH: 56
<212> TYPE: DNA
<213> ORGANISM: artificial sequence
<220> FEATURE:
<223> OTHER INFORMATION: ShRNA coding sequence

<400> SEQUENCE: 37
agtttgataa tgttggtgga agttaatatt catagcttcc accagcatta tcaaac      56

<210> SEQ ID NO 38
<211> LENGTH: 57
<212> TYPE: DNA
<213> ORGANISM: artificial sequence
<220> FEATURE:
<223> OTHER INFORMATION: ShRNA coding sequence

<400> SEQUENCE: 38
gcgccaatgg acaatattaa tgttaatatt catagcattg atattgtcca ttggcgc    57

<210> SEQ ID NO 39
<211> LENGTH: 57
<212> TYPE: DNA
<213> ORGANISM: artificial sequence
<220> FEATURE:
<223> OTHER INFORMATION: ShRNA coding sequence

<400> SEQUENCE: 39
gacttgaagg aacgtattaa tgttaatatt catagcatta gtacgttcct tcaagtc    57

<210> SEQ ID NO 40
<211> LENGTH: 57
<212> TYPE: DNA
<213> ORGANISM: artificial sequence
<220> FEATURE:
<223> OTHER INFORMATION: ShRNA coding sequence

<400> SEQUENCE: 40
gatacatctg tccttagtta tgttaatatt catagcataa ctgaggacag atgtatc    57

<210> SEQ ID NO 41
<211> LENGTH: 57
<212> TYPE: DNA
<213> ORGANISM: artificial sequence
<220> FEATURE:
<223> OTHER INFORMATION: ShRNA coding sequence

<400> SEQUENCE: 41
cgtgaagaag agggagagga agttaatatt catagctttc tcttcctctt cttcacg    57

<210> SEQ ID NO 42
<211> LENGTH: 57
<212> TYPE: DNA
<213> ORGANISM: artificial sequence
<220> FEATURE:
<223> OTHER INFORMATION: ShRNA coding sequence

<400> SEQUENCE: 42
cgaggtagag atcctaaata agttaatatt catagcttgt ttaggatctc tacctcg    57

<210> SEQ ID NO 43
<211> LENGTH: 57
<212> TYPE: DNA
<213> ORGANISM: artificial sequence
<220> FEATURE:
<223> OTHER INFORMATION: ShRNA coding sequence

<400> SEQUENCE: 43
ccgctggtgg attgtaatag tgttaatatt catagcatta ttacagtcca ccagcgg    57

<210> SEQ ID NO 44
<211> LENGTH: 57
<212> TYPE: DNA
<213> ORGANISM: artificial sequence
<220> FEATURE:
<223> OTHER INFORMATION: ShRNA coding sequence -continued

```
<400> SEQUENCE: 44
cctatcagag gccatctatt tgttaatatt catagcgaat aggtggcctc tgatagg        57

<210> SEQ ID NO 45
<211> LENGTH: 57
<212> TYPE: DNA
<213> ORGANISM: artificial sequence
<220> FEATURE:
<223> OTHER INFORMATION: ShRNA coding sequence

<400> SEQUENCE: 45
gccagtgatt atgagtttga agttaatatt catagcttca agctcataat cactggc        57

<210> SEQ ID NO 46
<211> LENGTH: 57
<212> TYPE: DNA
<213> ORGANISM: artificial sequence
<220> FEATURE:
<223> OTHER INFORMATION: ShRNA coding sequence

<400> SEQUENCE: 46
gccaccaagt tagataaaga agttaatatt catagcttct ttatctagct tggtggc        57

<210> SEQ ID NO 47
<211> LENGTH: 57
<212> TYPE: DNA
<213> ORGANISM: artificial sequence
<220> FEATURE:
<223> OTHER INFORMATION: ShRNA coding sequence

<400> SEQUENCE: 47
gctgatagtt gaagaaagaa agttaatatt catagctttc tttcttcaac tgtcagc        57
```

MOLECULAR TARGETS FOR SELECTIVE ERADICATION OF SENESCENT CELLS

CROSS REFERENCE TO RELATED APPLICATIONS

This application claims priority to U.S. provisional patent application No. 61/898,904, filed Nov. 1, 2013, the disclosure of which is incorporated herein by reference.

FIELD

The present invention relates generally to cancer, aging and age-related diseases, and prophylactic/therapeutic approaches to the same.

BACKGROUND

The scientific concept of aging and age-related diseases being caused by pathological secretion of accumulated senescent cells has been described in detail in the following: (Campisi, 1998; Davalos, Coppe, Campisi, & Desprez, 2010; Freund, Orjalo, Desprez, & Campisi, 2010; Laberge et al., 2012; Laberge, Awad, Campisi, & Desprez, 2011; Weyand, Fulbright, & Goronzy, 2003). This idea was experimentally tested by Baker et al. (Baker et al., 2011) who demonstrated using an artificial mouse-based model of premature aging the principle of possibility of reverting age-associated phenotypes by selective eradication of senescent cells. However, a recent attempt (believed to be the only of its kind) to identify such pharmacological agents failed to discover small molecules with the desired properties (Laberge et al., 2012).

The general decline of physiological function and increased frequency of specific diseases, such as cancer, Alzheimer's disease, diabetes type II, macular degeneration, chronic inflammation-based pathologies, etc. occur with aging. They are believed to be part of age-related syndrome caused by gradual accumulation in mammalian organism of so-called senescent cells that have undergone irreversible growth arrest in response to activation of oncogenes and/or oxidative stresses. Senescent cells are characterized by specific pattern of gene expression that includes production of a large number of bioactive secreted factors together forming a so-called "pathological secretory phenotype" contributing to general systemic poisoning of the organism that is manifested as one or more age-related syndromes. Selective eradication of senescent cells by pharmacological agents is, therefore, expected to prevent from and treat age-related diseases. However, development of drugs capable of selective killing of senescent cells has not been possible due to lack of knowledge of "Achilles heals" of senescent cells, namely the genes, expression of which are essential for the viability of senescent cells. Thus, there is an ongoing and unmet need to identify targets for selective eradication of senescent cells and for compositions and methods for prophylaxis and therapy of diseases correlated with expression of those targets. The present disclosure meets these and other needs.

SUMMARY OF THE DISCLOSURE

The present disclosure provides in one embodiment a method for selective partial or complete eradication of senescent cells in a mammal, and thus provides compositions and methods for selectively targeting and killing such cells. The method generally comprises inhibition of the expression of genes that are related to the senescent phenotype using methods which include but are not necessarily limited to pharmacological inhibition, or inhibition by using RNAi-mediated approaches. The suppression can include suppression of the expression of transcription, translation, or the function of the proteins encoded by any one or any combination of the genes described herein. The genes are selected from the list presented in Table 1, and any single and any combination of such genes can be targeted using the compositions and methods of the disclosure.

The method generally comprises inhibiting expression of the genes by interfering with RNA, and/or by interfering with the function of polypeptides encoded by the RNA, and or pathways in which such proteins are involved, such as the Integrin/Rac signaling pathway. The method in a general embodiment comprises contacting a cell which expresses one or more said genes with a composition comprising an agent capable of said inhibition. In various embodiments, the disclosure includes killing senescent cells that are irreversibly arrested and are accumulated with age in tissues of mammals. The senescent cells can be cells of connective or epithelial tissue, or irreversibly arrested melanocytes, or irreversibly arrested tumor cells (spontaneously or following radiation or chemotherapy), or other cells. In various embodiments, eradication of senescent cells comprises eradicating the cells systemically in the whole organism, organ-specifically (e.g., in the skin), or a tumor, such as following conventional cancer treatment by radiation or chemotherapy. The modulation of the cells can comprise a pharmacological inhibition of expression of genes from Table 1 or activity of their products, and can be achieved using any suitable means, including but not necessarily limited to RNAi (including siRNA or shRNA), micro-RNA or antisense oligonucleotide technologies, or inhibiting the activity or stability of the identified proteins encoded by the gene targets by specific small molecules, neutralizing antibodies or other specific biologics, or by using pharmacological agents developed to target (modulate activity or eliminate) any of the gene products listed in Table 1 for the purposes different than treatment or prophylaxis of aging or age-related diseases (e.g., treatment of cancer). In certain embodiments, the disclosure involves selective eradication of senescent cells performed with the purpose of preventing or treating aging and prolonging or restoring healthy physiological conditions in a mammal. For example, the selective eradication can be done to prevent or treat age-related diseases such as Alzheimer's disease, type II diabetes, macular degeneration, chronic inflammation-based pathologies (e.g., arthritis), and/or to prevent development of cancer types known to be associated with aging (e.g., prostate cancer, melanoma, lung cancer, colon cancer, etc.), and/or with the purpose to restore function and morphology of aging tissues (e.g., skin or prostate), and/or with the purpose to improve morphology of tissue impaired by accumulated senescent cells (e.g., cosmetic treatment of pigmented skin lesions), and/or with the purpose to improve the outcome of cancer treatment by radiation or chemotherapy, and/or with the purpose to prevent recurrent and metastatic disease in cancer patients by elimination of dormant cancer cells. The disclosure is suitable for prophylaxis and/or therapy of human and non-human animal diseases and ageing and age-related disorders.

It will be apparent from the foregoing that the present disclosure comprises a method for selectively killing senescent cells in a mammal comprising administering to the mammal at least one agent such that the expression of at least one gene selected from the genes presented in Table 1 is inhibited, and wherein the inhibition of such expression is lethal to the senescent cells. In embodiments, the inhibition of at least one gene is achieved by RNAi-mediated downregulation of mRNA encoded by the gene, and thus can be achieved using an shRNA, an siRNA. In embodiments, antisense oligonucleotides can be used. In embodiments the senescent cells are selected from irreversibly arrested cells present in connective tissue, epithelial tissue, and combinations thereof. In embodiments, the senescent cells are irreversibly arrested melanocytes, or irreversibly arrested tumor cells. In one example, the irreversibly arrested tumor cells are arrested subsequent to exposure to a chemotherapeutic agent or radiation. In one example, senescent cells are eliminated from a tumor subsequent to treatment of the mammal by radiation or chemotherapy. In one aspect the disclosure relates to the selective eradication of senescent cells is in a mammal suspected of having or at risk for developing an age-related disease, including but not necessarily limited to Alzheimer's disease, Type II diabetes, macular degeneration, or a disease comprising chronic inflammation, including but not necessarily limited to arthritis. In one aspect, the subject of the therapy of the present disclosure is in need of or is undergoing treatment for cancer, including but not necessarily limited to prostate cancer, melanoma, lung cancer, sarcoma, breast cancer, and colon cancer. In another aspect the individual is in need of therapy for tissue impaired by accumulated senescent cells, such as senescent cells that are present in a pigmented skin lesion. In an embodiment, administering an agent as described herein improves the outcome of a cancer treatment of a mammal. In embodiments, the cancer treatment is radiation or chemotherapy. In certain approaches, the mammal is in need of treatment for a metastatic cancer, and by practicing a method of this disclosure, dormant cancer cells in the mammal are killed. In certain embodiments, the lifespan of the mammal is increased subsequent to administering of an agent as disclosed herein. In certain embodiments, the agent delivered to the mammal targets a gene selected from ITGAV, RAC1, ARHGAP1, RAPGEF1, CRKL, NCKAP1, CDC42, CAPNS2, EBP, FGF1, ISG20, KITLG, LPHN1, MAG, MEF2C, OSBPL3, PFN1, POU5F1, PPP1CB, PRKRA, and combinations thereof. In certain embodiments, the mammal that is a subject of the prophylactic and/or therapeutic methods described herein in a human. In other embodiments the subject is a non-human mammal.

DETAILED DESCRIPTION

Figure 1:
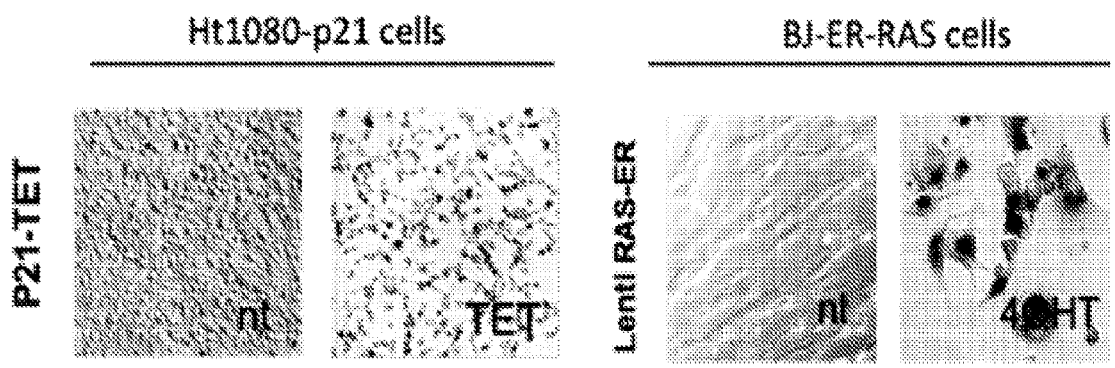
FIG. 1. Inducible models of cellular senescence used for the screening of the human 27K Pathway DECIPHER shRNA library. The HT1080-p21 cells carry tetracyclin-regulated p21 (WAF1) protein. Treatment of the cells with doxycyclin for 4 days induce p21 and a stable senescence state. Activation of mutant HRAS fused to estrogen receptor in immortalized human foreskin diploid fibroblasts BJ was achieved by addition of hydroxitamoxifen to the culture media for 4 days.
Figure 2:
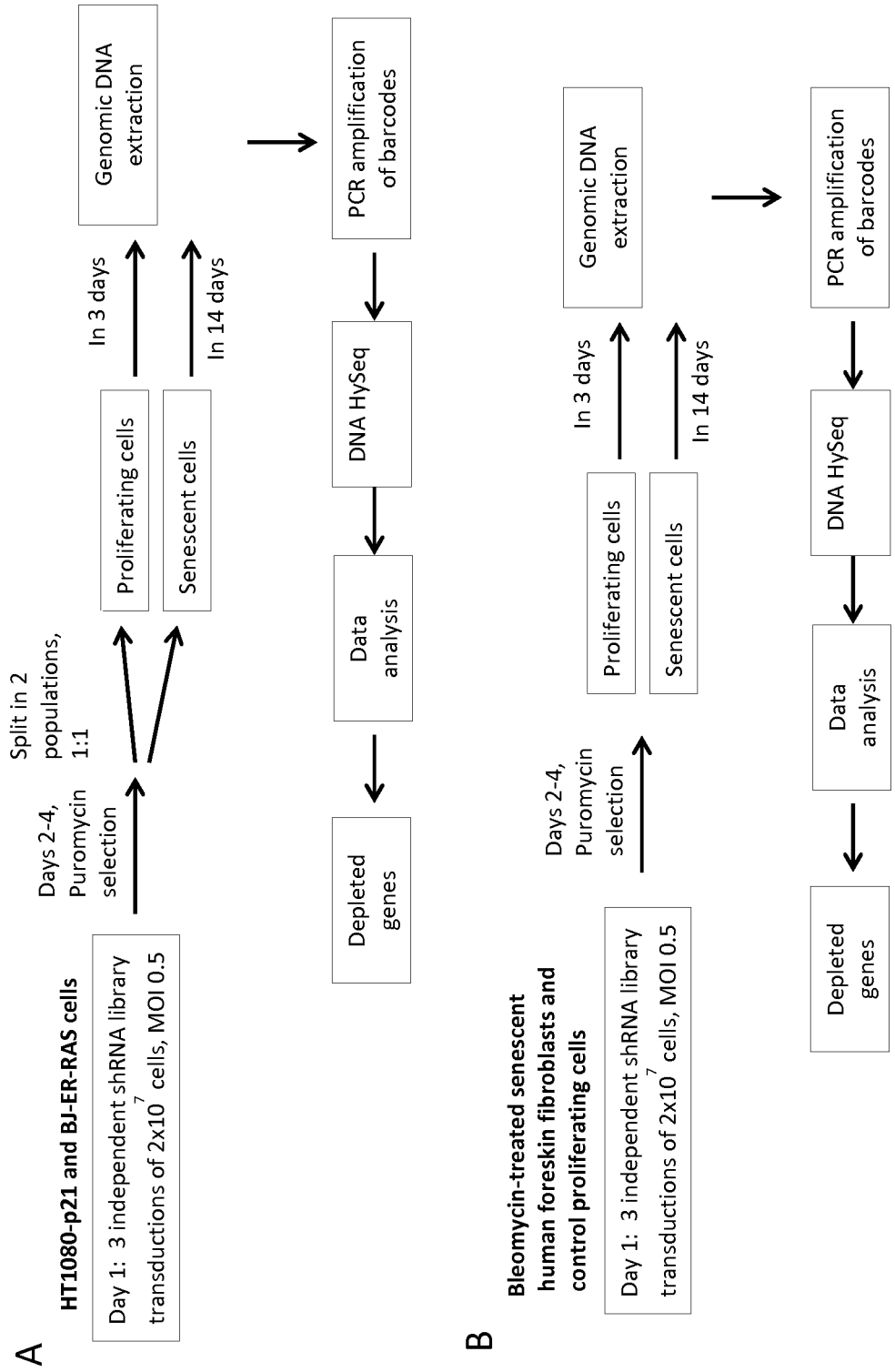
FIG. 2. shRNA library Screening Flowcharts. Panel A provides a flow chart showing the work flow in cellular models with inducible oncogene (HRAS) or tumor suppressor (p21-WAF1). The cells were transduced with the shRNA library, selected with puromycin and divided into two populations: one population was changed to a senescent state, in the second population the cells continued proliferatation or remained confluent. In panel B senescence of human foreskin fibroblasts was induced by treatment with bleomycin. Populations of senescent and contact-inhibited quiescent cells were independently transduced with shRNA library and selected for surviving cells. At the end of viability selection all cells were lysed, followed by extraction of genomic DNA. shRNA constructs barcodes were PCR-amplified and sequenced. Statistical analysis of the data allowed identification of shRNA constructs that were depleted during selection.

The present disclosure is related generally to our development of a functional genetic approach for the isolation and identification of senescence-specific molecular targets.

As will be apparent to those skilled in the art from the description, we have identified molecular targets that are present in and are believed to be important for viability of senescent cells. "Cellular senescence" and "senescent cells" refers to the essentially irreversible growth arrest that occurs when cells that can divide encounter oncogenic stress or DNA damage. See, for example, Rodier F, Campisi J. Four faces of cellular senescence. J Cell Biol. 2011 February. In embodiments, "senescent cells" as the term is used in this disclosure refers to cells which express a marker or combination of markers that are characteristic of senescence. Such markers include but are not necessarily limited to the p16INK4a tumor-suppressor protein, and increased expression relative to a reference, such as a non-senescent cell, in the levels of DNA-damage response (DDR) markers, as well as the cell cycle inhibitors $p16^{INK4A}$, $p15^{INK4B}$, $p21^{CIP1}$, and p53. DEC1, DCR2 (Collado M, et al. 2005. Tumour biology: Senescence in premalignant tumours. Nature 436: 642), and PAI1 (Goldstein S, et al, 1994. Overexpression of plasminogen activator inhibitor type-1 in senescent fibroblasts from normal subjects and those with Werner syndrome. J Cell Physiol 161: 571-579) have also been used as senescence biomarkers (Collado M, Serrano M. 2010. Senescence in tumours: Evidence from mice and humans. Nat Rev Cancer 10: 51-57). In one embodiment, senescent cells are SA-beta-Gal (senescence-associated beta galactosidase) positive.

It is expected that prophylactic and/or therapeutic modulation of one or more of these targets will result in a benefit to the individual in which the modulation is brought about. Thus, the disclosure includes modulating any one, or any combination of the molecular targets identified herein.

Modulating includes reducing the amount of the target, or a polypeptide encoded by the target, and/or factors in a biochemical pathway in which the target plays a role with respect to cellular senescence. In one embodiment the disclosure comprises a composition comprising an agent that is capable of downregulating the amount and/or expression of any one or any combination of the targets disclosed herein. The disclosure provides a method of selectively targeting/inhibiting the growth of/identifying/killing senescent cells as is more fully described herein and in the claims. The method comprises administering to an individual a composition comprising an agent that can disrupt the function of one or a combination of the targets described herein. In one embodiment, the disruption of the function of one or a combination of the targets described herein results in an anti-cancer effect, and/or an anti-aging effect. Anti-aging effects include but are not limited to prophylaxis and/or therapy of one or more age-related diseases. Thus, in various embodiments, the method comprises administering to an individual in need thereof an effective amount of a composition comprising one or more agent(s) capable of disrupting the function of one or more of the targets identified herein. In one embodiment, the individual to whom a composition of the disclosure is administered is an individual who is at risk for, is suspected of having or has been diagnosed with cancer, and/or an age-related disease.

Any agent that can disrupt the function of one or more of the targets described herein can be provided as a pharmaceutical preparation, such as in a composition comprising a pharmaceutically acceptable carrier. The compositions can be administered via any suitable route and in any suitable formulation. Thus, intravenous, intramuscular, subcutaneous, oral, intraperitoneal, and all other methods and formulations for delivery to an individual are encompassed.

In one aspect, the disclosure includes reducing target mRNA and/or inhibiting its transcription, and as a result reducing the target protein, in senescent cells. Target mRNAs are mRNAs that are encoded by any of the genes described herein. The sequence of the target mRNAs is readily accessible from the GenBank accession numbers described in Table 1. Reducing target RNA comprises in various embodiments introducing into the senescent cells a polynucleotide that can inhibit translation of target mRNA, and/or can participate in and/or facilitate RNAi-mediated reduction of target mRNA. In one embodiment, an antisense polynucleotide is used to inhibit translation of target mRNA. Antisense nucleic acids can be DNA or RNA molecules that are complementary to at least a portion of the target mRNA. In embodiments, oligomers of about fifteen nucleotides, and/or those that hybridize to the AUG initiation codon will be particularly efficient. The polynucleotides described herein for use in targeting target mRNA can in certain embodiments be modified, such as to be resistant to nucleases.

In another aspect the disclosure includes RNAi-mediated reduction in target mRNA. RNAi-based inhibition can be achieved using any suitable RNA polynucleotide that is targeted to target mRNA. In embodiments, a single stranded or double stranded RNA, wherein at least one strand is complementary to the target mRNA, can be introduced into the cell to promote RNAi-based degradation of target mRNA. In another embodiment, microRNA (miRNA) targeted to the target mRNA can be used. In another embodiment, a ribozyme that can specifically cleave target mRNA can be used. In yet another embodiment, small interfering RNA (siRNA) can be used. siRNA (or ribozymes) can be introduced directly, for example, as a double stranded siRNA complex, or by using a modified expression vector, such as a lentiviral vector, to produce an shRNA. As is known in the art, shRNAs adopt a typical hairpin secondary structure that contains a paired sense and antisense portion, and a short loop sequence between the paired sense and antisense portions. shRNA is delivered to the cytoplasm where it is processed by DICER into siRNAs. siRNA is recognized by RNA-induced silencing complex (RISC), and once incorporated into RISC, siRNAs facilitate cleavage and degradation of targeted mRNA. In embodiments, an shRNA polynucleotide used to suppress TARGET expression can comprise or consist of between 45-100 nucleotides, inclusive, and including all integers between 45 and 100. The portion of the shRNA that is complementary to the target mRNA mRNA can be from 21-29 nucleotides, inclusive, and including all integers between 21 and 29.

For delivering siRNA via shRNA, modified lentiviral vectors can be made and used according to standard techniques, given the benefit of the present disclosure. Further, lentiviral vectors expressing shRNAs targeted to many human mRNAs are commercially available, and use of shRNA to inhibit expression of TARGET has already been demonstrated in HeLaP4 cells (Vandekerckhove, et al.). Additionally, custom siRNAs or shRNA can be obtained from, for example Thermo-Dharmacon or Cellecta for transient transfection resulting in temporary reduction in TARGET levels. Alternatively, lentiviral constructs expressing human PSIP11 targeted shRNA can be obtained from Thermo Dharmacon. These lentiviruses are capable of stably and permanently infecting target cells, such as by integrating into a chromosome in the Senescent cells cells.

In another aspect, the disclosure includes disrupting the target gene such that target mRNA and protein are not expressed. In one embodiment, the target gene can be disrupted by targeted mutagenesis. In embodiments, targeted mutagenesis can be achieved by, for example, targeting a CRISPR (clustered regularly interspaced short palindromic repeats) site in the target gene. So-called CRISPR systems designed for targeting specific genomic sequences are known in the art and can be adapted to disrupt the target gene for making modified cells encompassed by this disclosure. In general, the CRIPSR system includes one or more expression vectors encoding at least a targeting RNA and a polynucleotide sequence encoding a CRSPR-associated nuclease, such as Cas9, but other Cas nucleases can be used. CRISPR systems for targeted disruption of mammalian chromosomal sequences are commercially available and can be adapted to disrupt the target1 gene in senescent cells given the benefit of this disclosure.

In embodiments, a targeting RNA encoded by the CRISPR system can be a CRISPR RNA (crRNA) or a guide RNA, such as sgRNA. The sequence of the targeting RNA has a segment that is the same as or complementarity to any CRISPR site in the target gene. In this regard, the target sequence comprises a specific sequence on its 3' end referred to as a protospacer adjacent motif or "PAM". In an embodiment a CRISPR Type II system is used, and the target sequences therefore conform to the well-known N12-20NGG motif, wherein the NGG is the PAM sequence. Thus, in embodiments, a target RNA will comprise or consist of a segment that is from 12-20 nucleotides in length which is the same as or complementary to a DNA target sequence (a spacer) in the target gene. The 12-20 nucleotides directed to the spacer sequence will be present in the targeting RNA, regardless of whether the targeting RNA is a crRNA or a guide RNA. In embodiments, a separate trans-activating crRNA (tracrRNA) can be used to assist in maturation of a crRNA targeted to the PSIP1 gene. Introduction a CRISPR system into senescent cells will result in binding of a targeting RNA/Cas9 complex to the target target sequence so that the Cas9 can cut both strands of DNA causing a double strand break. The double stranded break can be repaired by non-homologous end joining DNA repair, or by a homology directed repair pathway, which will result in either insertions or deletions at the break site, or by using a repair template to introduce mutations, respectively. Double-stranded breaks can also be introduced into the PSIP1 gene by expressing Transcription activator-like effector nucleases (TALENs) in the senescent cells cells. TALENs are artificial restriction enzymes generated by fusing a TAL effector DNA binding domain to a DNA cleavage domain and are known in the art and can be adapted for use in embodiments of this disclosure. In yet another approach, zinc-finger nucleases (ZFNs) can be expressed in the senescent cells to target the gene of interest. ZFNs are artificial restriction enzymes produced by fusing a zinc finger DNA-binding domain to a DNA-cleavage domain. ZF domains can be designed to target the gene DNA sequences where the zinc-finger nucleases cleave the sequence, thereby disrupting the gene.

The targets for which the compositions and methods of the disclosure are directed include any one and combination of targets described herein, which include but are not necessarily limited to RNA and proteins involved in the Integrin/Rac signaling pathway. This includes but is not necessarily limited to ITGAV, RAC1, ARHGAP1, RAPGEF1, CRKL, NCKAP1, CDC42, and combinations thereof, in senescent cells.

In certain embodiments, the targets are defined by the list of targets set forth in Table 1. Table 1 includes accession numbers for these targets. The sequence of each of the targets associated with each of these accession numbers is incorporated herein by reference, as those sequences existed under the accession numbers as of the filing date of this application or patent.

TABLE 1

| Symbol | Name | GeneID | GenBank Number |
|---|---|---|---|
| APC | adenomatous polyposis coli | 324 | NM_000038 |
| ARHGAP1 | Rho GTPase activating protein 1 | 392 | NM_004308 |
| AXL | AXL receptor tyrosine kinase | 558 | NM_001699 |
| BCL2L1 | BCL2-like 1 | 598 | NM_001191 |
| CAPNS2 | calpain, small subunit 2 | 84290 | NM_032330 |
| CDC42 | cell division cycle 42 (GTP binding protein, 25 kDa) | 998 | NM_001039802 |
| CDKN2C | cyclin-dependent kinase inhibitor 2C (p18, inhibits CDK4) | 1031 | NM_001262 |
| CLYBL | citrate lyase beta like | 171425 | NM_206808 |
| COPG1 | coatomer protein complex, subunit gamma 1 | 22820 | NM_016128 |
| CRKL | v-crk sarcoma virus CT10 oncogene homolog (avian)-like | 1399 | NM_005207 |
| DGKA | diacylglycerol kinase, alpha 80 kDa | 1606 | NM_001345 |
| EBP | emopamil binding protein (sterol isomerase) | 10682 | NM_006579 |
| FGF1 | fibroblast growth factor 1 (acidic) | 2246 | NM_000800 |
| GBA3 | glucosidase, beta, acid 3 (cytosolic) | 57733 | NM_001128432 |
| GIT2 | G protein-coupled receptor kinase interacting ArfGAP 2 | 9815 | NM_001135213 |
| IGF1 | insulin-like growth factor 1 (somatomedin C) | 3479 | NM_000618 |
| ISG20 | interferon stimulated exonuclease gene 20 kDa | 3669 | NM_002201 |
| ITGAV | integrin, alpha V | 3685 | NM_001144999 |
| KITLG | KIT ligand | 4254 | NM_000899 |
| LCMT2 | leucine carboxyl methyltransferase 2 | 9836 | NM_014793 |
| LPHN1 | latrophilin 1 | 22859 | NM_001008701 |
| MADCAM1 | mucosal vascular addressin cell adhesion molecule 1 | 8174 | NM_130760 |
| MAG | myelin associated glycoprotein | 4099 | NM_080600 |
| MAP3K14 | mitogen-activated protein kinase kinase kinase 14 | 9020 | NM_003954 |
| MEF2C | myocyte enhancer factor 2C | 4208 | NM_001131005 |
| MTHFD2 | methylenetetrahydrofolate dehydrogenase (NADP+ dependent) 2 | 10797 | NM_006636 |
| NAIP | NLR family, apoptosis inhibitory protein | 4671 | NM_004536 |
| NAPG | N-ethylmaleimide-sensitive factor attachment protein, gamma | 8774 | NM_003826 |
| NCKAP1 | NCK-associated protein 1 | 10787 | NM_013436 |
| NNMT | nicotinamide N-methyltransferase | 4837 | NM_006169 |
| OSBPL3 | oxysterol binding protein-like 3 | 26031 | NM_015550 |
| PARK2 | parkinson protein 2, E3 ubiquitin protein ligase (parkin) | 5071 | NM_004562 |
| PFN1 | profilin 1 | 5216 | NM_005022 |
| PMS2 | PMS2 postmeiotic segregation increased 2 (*S. cerevisiae*) | 5395 | NM_000535 |
| POU5F1 | POU class 5 homeobox 1 | 5460 | NM_001173531 |
| PPP1CB | protein phosphatase 1, catalytic subunit, beta isozyme | 5500 | NM_002709 |
| PRKRA | protein kinase, interferon-inducible double stranded RNA dependent activator | 8575 | NM_001139517 |
| PRPF19 | PRP19/PSO4 pre-mRNA processing factor 19 homolog (*S. cerevisiae*) | 27339 | NM_014502 |
| PRTG | protogenin | 283659 | NM_173814 |
| RAC1 | ras-related C3 botulinum toxin substrate 1 | 5879 | NM_006908 |
| RAPGEF1 | Rap guanine nucleotide exchange factor (GEF) 1 | 2889 | NM_005312 |
| RET | ret proto-oncogene | 5979 | NM_020630 |
| VIT | vitrin | 5212 | NM_001177969 |
| WEE1 | WEE1 homolog (*S. pombe*) | 7465 | NM_001143976 |
| YAP1 | Yes-associated protein 1 | 10413 | NM_001130145 |
| YWHAE | tyrosine 3-monooxygenase/tryptophan 5-monooxygenase activation protein, epsilon | 7531 | NM_006761 |

We utilized the Module 1 sub-library of the human Druggable Genome and Pathway Decipher (27K hDGPD) library of pooled bar-coded lentiviral shRNA clones that target approximately 5,000 human transcripts. The library consists of redundant sets of 5-6 shRNAs per targeted gene in a lentiviral vector that directs constitutive expression of both the mCherry red fluorescent protein (RFP) and puromycin resistance (puroR) genes from the ubiquitin promoter (to enable selection of transduced cells) and expression of inserted shRNAs from the U6 RNA pol III promoter. The vector backbone contains unique 18 bp "barcodes" that identify each individual shRNA in the library and make the library amenable to the high-throughput Next-Generation Sequencing (NGS). The 27K hDGPD library and screening services were provided by Cellecta, To identify molecular targets in senescent cells originating from connective tissue the lentiviral human 27K Pathway DECIPHER shRNA library (Module 1) was transduced in triplicates into human fibrosarcoma cells HT1080 cells carrying inducible tetracycline-regulated p21/WAF protein (induction of senescence is shown in FIG. 1) so that each shRNA was delivered into 100 cells at MOI 0.5 (see screening scheme in the Screen Flowcharts).

On day two, the transduced cells were selected with puromycin following by induction of p21/WAF1 on day four by addition of doxycycline to the growth media for four days. The p21/WAF1 arrested cells were cultured for 4 days to develop senescent phenotype after which p21/WAF1 induction was reverted by removal of doxycycline and cells were incubated for additional 10 days in the regular growth media. The control cells were not arrested (no p21/WAF1 induction) and continue proliferation. On day 18 the cells were harvested for isolation of genomic DNA. The unique bar-codes identifying each shRNA sequence were PCR-amplified as a pool and subjected to high throughput sequencing on the Illumina sequencing platform. To identify genes that are critical for viability of senescent cells we concentrated on characterization of genes whose inhibition sensitizes senescent cells to death leading to a depleted representation of shRNA-specific barcodes comparing to non-senescent control. In the primary screening of the HT1080-p21 cells 257 barcodes were identified with reduced abundance in senescent cells. These barcodes represent 187 candidate gene targets. We prioritized the hits according to combined selection score, which takes into account degree of depletion and presence of >1 shRNA from 6 specific for a particular gene, and selected top 65 depleted targets for individual confirmation. For validation and potentially further analysis, we focused on hits that were (i) depleted at least 2-fold in at least 2 out of 3 biological replicates and (ii) represented in the depleted shRNA pools by three or more independent shRNAs.

A similar approach was used to identify molecular targets in Ras-induced senescent cells using the same DECIPHER shRNA library, 27K Pathway Decipher shRNA library, Module 1. The library was transduced into human foreskin fibroblasts BJ/ET/RASV12ER cells carrying 4-OH-tamoxifen (4-OHT)-inducible oncogene H-RasV12. Treatment of the cells on day 3 with 4-OHT for two weeks induced oncogenic Ras-mediated cell cycle arrest following by senescence. The cells were harvested on day 18, genomic DNA was isolated, and the bar-codes uniquely identifying each shRNA sequence were PCR-amplified as a pool and sequenced.

The results of the high throughput sequencing demonstrated that we were able to isolate drug targets for sensitization of RAS-arrested cells to cell death. Representation of shRNAs targeting these genes is reduced relative to the control. Several of the isolated drug targets belong to RET signaling pathway, indicating that known inhibitors of this pathway may be explored for isolation of drugs inducing cell death in senescent cells.

This approach allowed for isolation of drug targets enabling selective elimination of senescent cells. By comparing the infected populations with and without induction of p21 and RAS, we are able to identify shRNAs differentially toxic for the senescent cells.

Similar approach has been used for the screening of genome-wide shRNA library using DNA-damage senescence model based on bleomycin-treated human diploid foreskin fibroblasts (NDF).

Figure 3:
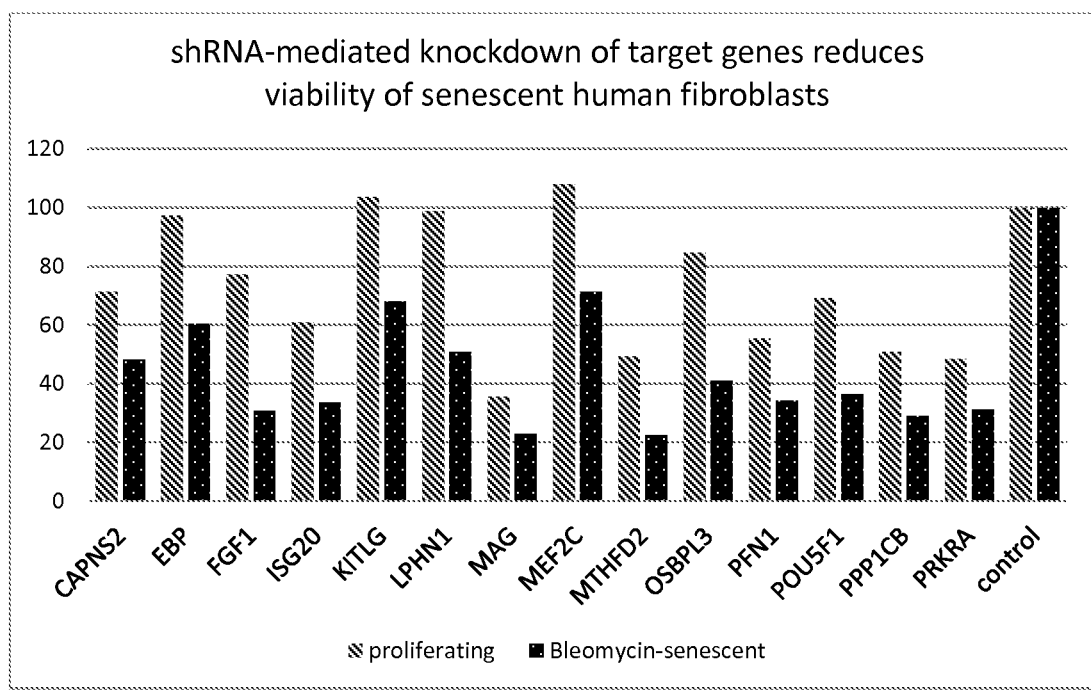
FIG. 3. Example of targeted genes where downregulation with shRNA resulted in decreased viability of senescent human foreskin fibroblasts pre-treated with bleomycin.
Figure 4:
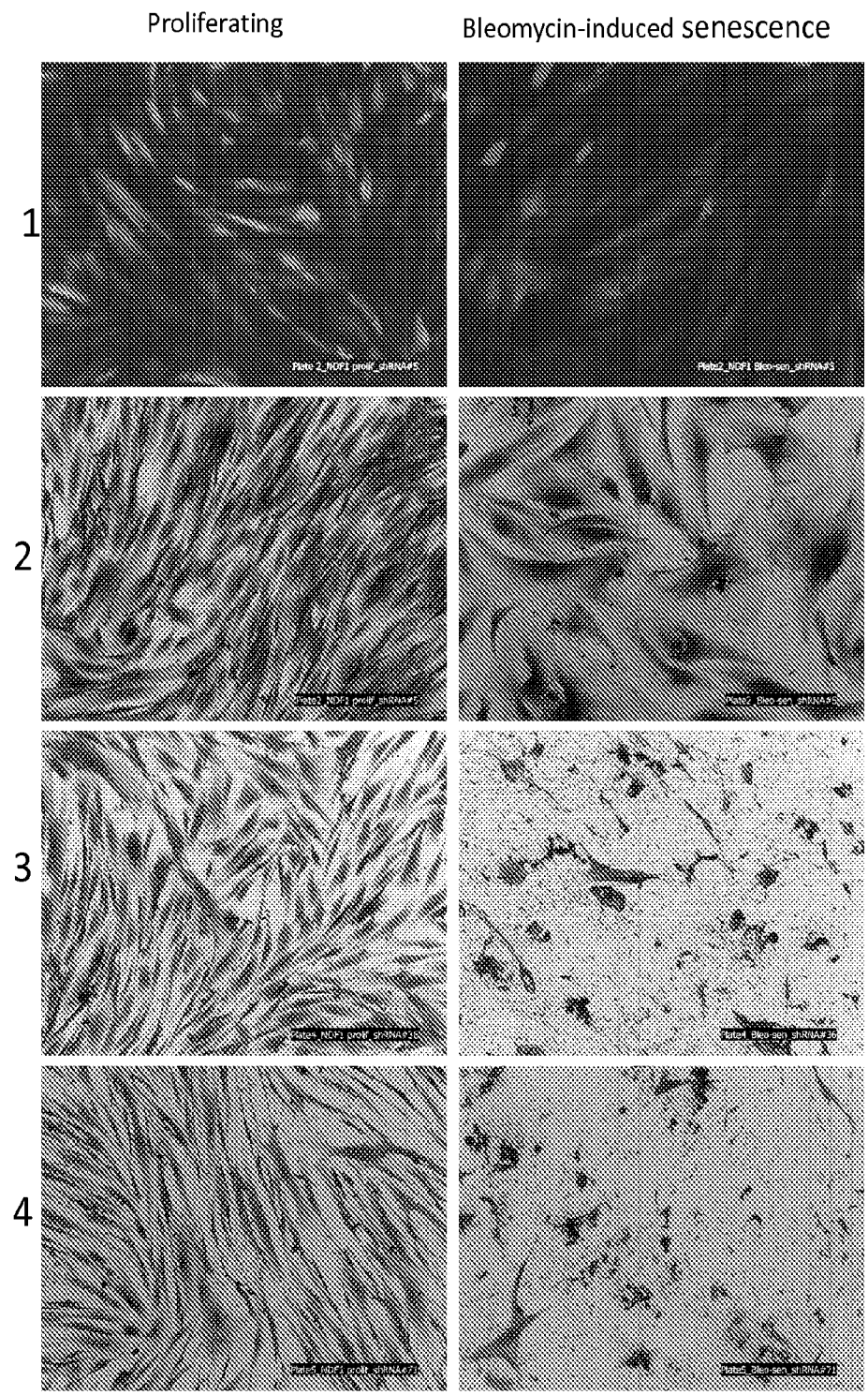
FIG. 4. Effect of selected shRNAs on viability of proliferating and senescent human neonatal dermal fibroblasts. Senescence was induced by treatment with bleomycin (10 μg/ml) for 24 hr followed by incubation for 10 days to establish senescent phenotype. (1) The proliferating and senescent cells were transduced with lentiviruses carrying both shRNA and mCherry constructs. Transduced cells were selected with puromycin for 72 hours and the presence of shRNA construct was confirmed by microscopic detection of mCherry fluorescence (see example of mCherry fluorescence in FIG. 4, panel 1). In 8 days for proliferating and 20 days for senescent cells, the cells were stained with crystal violet dye. The images of the live/dead cells were obtain using a digital camera (panels 2-4). (2) Control luciferase shRNA construct had no cytotoxic effect on the proliferating or senescent cells. Panels 3-4 demonstrate examples of target genes FGF1 (3) and POU5F1 (4) that are critical for viability of senescent cells.

To confirm universal activity of identified target genes across different senescence models 60 candidate shRNA identified in all primary screenings were transduced to a secondary models of senescence: human diploid dermal fibroblasts induced to senescence by bleomycin treatment (DNA-damage induction) or senescence was induced by replicative exhaustion (replicative senescence). Senescent cell specific cytotoxicity for several representative shRNA clones is shown in FIGS. 3 and 4. The full list of the genes representing drug targets is shown in Table 1.

Many of the isolated drug targets belong to Integrin/Rac signaling pathway (ITGAV, RAC1, ARHGAP1, RAPGEF1, CRKL, NCKAP1, CDC42), indicating that known inhibitors of this pathway may be explored for isolation of drugs inducing cell death in senescent cells. ITGAV is an integrin alpha V (vitronectin receptor, alpha). I-domain containing integrin alpha V undergoes cleavage to yield disulfide-linked heavy and light chains, that combine with multiple integrin beta chains to form different integrins, and associating beta chains can interact with extracellular matrix ligands. The alpha V beta 3 integrin is the Vitronectin receptor (VNR). CRKL is a v-crk sarcoma virus CT10 oncogene homolog. It is a protein kinase containing SH2 and SH3 (src homology) domains, which has been shown to activate the RAS and JUN, substrate of the BCR-ABL tyrosine kinase. RAC1 is a Ras-related C3 botulinum toxin substrate 1 GTPase, which belongs to the RAS superfamily of small GTP-binding proteins. It regulates a diverse array of cellular events, including the control of cell growth, cytoskeletal reorganization, and the activation of protein kinases. RAPGEF1 is a Rap guanine nucleotide exchange factor (GEF) 1. It transduces signals from CRK by binding the SH3 domain of CRK, and activating several members of the Ras family of GTPases. This is a signaling cascade that may be involved in apoptosis, integrin-mediated signal transduction, and cell transformation. NCKAP1 is an NCK-associated protein 1, which interacts with Nck and may be involved in the downstream signaling of Nck. It is involved in RAC signaling and regulation of actin polymerization. ARHGAP1 is aRho GTPase activating protein involved in positive regulation of Rac and Rho GTPase activity. CDC42 is a cell division cycle 42 small GTPase of the Rho-subfamily, which regulates signaling pathways that control diverse cellular functions including cell morphology, migration, endocytosis and cell cycle progression, and actin polymerization through its direct binding to Neural Wiskott-Aldrich syndrome protein (N-WASP), which subsequently activates Arp2/3 complex.

Validation of individual depleted shRNA hits in the primary and secondary models of senescence was performed as follows. To confirm putative target genes and characterize toxicity profiles of isolated shRNAs, 90 depleted or enriched senescence-specific shRNAs identified in the pooled format primary screens were synthesized individually and cloned into pRSI-U6 wt-Ubi-mCherry-2A-P lentiviral vector. Three secondary models of senescence were used to validate 90 individual shRNA clones: HT1080-p21 (carry doxycylin inducible p21WAF), WI-38 (replicative senescence at a late passage), BJ-ER-RAS (carry tamoxifen iducible HRAS) and bleomycin-treated human diploid foreskin fibroblasts. The senescent cells were infected at high MOI (MOI=3) and in 7 days their viability was measured using Resazurin assay. The delivery of single shRNAs to the cells was confirmed by RFP expression provided by the vector. The criteria for selection of confirmed target gene were: (i) depletion at least 2-fold in at least 2 out of 3 biological replicates and (ii) two or more (up to 6-8) independent shRNAs decrease viability of senescent cells in at least one model. The combined list of confirmed depleted shRNA clones is presented in Table 2. Those skilled in the art will recognize that there are a wide variety of polynucleotide sequences that will be suitable for use RNAi and antisense mediated downregulating of each of the target genes described herein. In particular, the list of shRNA sequences

TABLE 2

| Gene | shRNA coding sequences in sense orientation, 5' to 3' |
|---|---|
| APC | GCCAACAAAGTCATCATGTAAGTTAATATTCATAGCT TACGTGATGACTTTGTTGGC (SEQ ID NO: 1) |
| ARHGAP1 | GCATCCAACCATGTTTATCAAGTTAATATTCATAGCT TGATGAACATGGTTGGATGC (SEQ ID NO: 2) |
| AXL | CTGGGTGGGGATGAATAGGATGTTAATATTCATAGCA TCCTGTTCATCCTCACCCAG (SEQ ID NO: 3) |
| BCL2L1 | GCTCATTCTTCAGTTGGAAATGTTAATATTCATAGCA TTTCCGACTGAAGAGTGAGC (SEQ ID NO: 4) |
| C12orf77 | CACTGGGAGTAAATAAGGGAAGTTAATATTCATAGCT TCCCTTGTTTGCTCCCAGTG (SEQ ID NO: 5) |
| CAPNS2 | GCCTGATTCAAGTGTTTATCAGTTAATATTCATAGCT GATAGACACTTGAATCAGGC (SEQ ID NO: 6) |
| CDC42 | CCTGATATCCTACACAATAAAGTTAATATTCATAGCT TTGTTGTGTAGGATATCAGG (SEQ ID NO: 7) |
| CDKN2C | TGGACACTTTACAGACTTTGTGTTAATATTCATAGCG CAAAGTCTGTAAAGTGTCCA (SEQ ID NO: 8) |
| CLYBL | GCCTTTGGTGTTCAAGCTATAGTTAATATTCATAGCT ATGGCTTGGAGACCAAAGGC (SEQ ID NO: 9) |
| COPG1 | CCCACATCCTCACTAAGATTTGTTAATATTCATAGCG AATCTTGGTGAGGATGTGGG (SEQ ID NO: 10) |
| CRKL | CGTGAAAGTCATAAGGATGAAGTTAATATTCATAGCT TCATCCTTGTGACTTTCACG (SEQ ID NO: 11) |
| DGKA | GCTAAATATGTCTAAGGAGATGTTAATATTCATAGCA TCTCCTTGGACATATTTAGC (SEQ ID NO: 12) |
| EBP | CTGGACAACTTTGTACTTAATGTTAATATTCATAGCA TTAGGTACAAAGTTGTCCAG (SEQ ID NO: 13) |
| FGF1 | CCTGATAACAAGTAAGGATATGTTAATATTCATAGCA TATCCTTGCTTGTTATCAGG (SEQ ID NO: 14) |
| GBA3 | CAGACTGGTGATGTAGTTTGTGTTAATATTCATAGCA CAAGCTACATCGCCAGTCTG (SEQ ID NO: 15) |
| GIT2 | ATAACGGTGCTAACTCTATATGTTAATATTCATAGCA TATAGAGTTAGCACCGTTA (SEQ ID NO: 16) |
| IGF1 | GCTGAGTTGGTGGATGTTCTTGTTAATATTCATAGCA AGAGCATCCACCAGCTCAGC (SEQ ID NO: 17) |
| ISG20 | GCACGACTTCTAGGCATTGAAGTTAATATTCATAGCT TCAGTGCCTGGAAGTCGTGC (SEQ ID NO: 18) |
| ITGAV | CTCTGTTGTATATCCTTCATTGTTAATATTCATAGCA ATGAAGGATATACAACAGAG (SEQ ID NO: 19) |
| KITLG | GCAGGAATCGTGTGATTAATAGTTAATATTCATAGCT ATTAGTCACACGATTCCTGC (SEQ ID NO: 20) |
| LCMT2 | GATCAATTTGACTACAGGATTGTTAATATTCATAGCA ATCCTGTAGTCAAATTGATC (SEQ ID NO: 21) |
| LPHN1 | GCTGGTGGTTTAAGGGTTGGAGTTAATATTCATAGCT TCAACCTTTAAACCACCAGC (SEQ ID NO: 22) |
| MADCAM1 | CCACCAGCTTCTTTGAGGTTTGTTAATATTCATAGCA AGCCTCAGAGAAGCTGGTGG (SEQ ID NO: 23) |
| MAG | GTGTGGTTGAGAACTAGTATGGTTAATATTCATAGCC ATACTGGTTCTCAGCCACAC (SEQ ID NO: 24) |
| MAP3K14 | GTGTGAGAATAGCTAAGAGTTGTTAATATTCATAGCA ACTCTTGGCTATTCTCACAC (SEQ ID NO: 25) |
| MEF2C | GCCTCAGTGATATAGTATAAAGTTAATATTCATAGCT TTATACTGTATCACTGAGGC (SEQ ID NO: 26) |
| MTHFD2 | GCAGTTGAAGAAACATACAATGTTAATATTCATAGCA TTGTATGTTTCTTCAACTGC (SEQ ID NO: 27) |
| NAIP | CGTGGTGGAGATTGCTAAAGTGTTAATATTCATAGCA CTTTGGCAATTTCCACCACG (SEQ ID NO: 28) |
| NAPG | GCAAGTTGGAATGATGTTGAAGTTAATATTCATAGCT TCAACATCATTCCAGCTTGC (SEQ ID NO: 29) |
| NCKAP1 | CCTCTCAATCAAGATATTCAAGTTAATATTCATAGCT TGAGTATCTTGATTGAGAGG (SEQ ID NO: 30) |
| NNMT | CTGGTTTCTGGAGGAAAGAGGGTTAATATTCATAGCT CTCTTTCCTCCAGAAGCCAG (SEQ ID NO: 31) |
| OSBPL3 | GAAGCGTAGCAGTATATTAAAGTTAATATTCATAGCT TTGATATACTGCTACGCTTC (SEQ ID NO: 32) |
| PARK2 | CACCTACCTAGTGACTATGATGTTAATATTCATAGCA TCATGGTCACTGGGTAGGTG (SEQ ID NO: 33) |
| PFN1 | GCATGGATCTTTGTACTAAGAGTTAATATTCATAGCT CTTGGTACGAAGATCCATGC (SEQ ID NO: 34) |
| PMS2 | CCAGGAAGATACTGGATGTAGGTTAATATTCATAGCT TACATCCGGTATCTTCCTGG (SEQ ID NO: 35) |
| POU5F1 | TCATTCACTAAGGAAGGAATTGTTAATATTCATAGCA ATTCCTTCCTTAGTGAATGA (SEQ ID NO: 36) |
| PPP1CB | AGTTTGATAATGTTGGTGGAAGTTAATATTCATAGCT TCCACCAGCATTATCAAAC (SEQ ID NO: 37) |
| PRKRA | GCGCCAATGGACAATATTAATGTTAATATTCATAGCA TTGATATTGTCCATTGGCGC (SEQ ID NO: 38) |
| PRPF19 | GACTTGAAGGAACGTATTAATGTTAATATTCATAGCA TTAGTACGTTCCTTCAAGTC (SEQ ID NO: 39) |
| PRTG | GATACATCTGTCCTTAGTTATGTTAATATTCATAGCA TAACTGAGGACAGATGTATC (SEQ ID NO: 40) |
| RAC1 | CGTGAAGAAGAGGGAGAGGAAGTTAATATTCATAGCT TTCTCTTCCTCTTCTTCACG (SEQ ID NO: 41) |

TABLE 2-continued

| Gene | shRNA coding sequences in sense orientation, 5' to 3' |
|---|---|
| RAPGEF1 | CGAGGTAGAGATCCTAAATAAGTTAATATTCATAGCT TGTTTAGGATCTCTACCTCG (SEQ ID NO: 42) |
| RET | CCGCTGGTGGATTGTAATAGTGTTAATATTCATAGCA TTATTACAGTCCACCAGCGG (SEQ ID NO: 43) |
| VIT | CCTATCAGAGGCCATCTATTTGTTAATATTCATAGCG AATAGGTGGCCTCTGATAGG (SEQ ID NO: 44) |
| Wee1 | GCCAGTGATTATGAGTTTGAAGTTAATATTCATAGCT TCAAGCTCATAATCACTGGC (SEQ ID NO: 45) |
| YAP1 | GCCACCAAGTTAGATAAAGAAGTTAATATTCATAGCT TCTTTATCTAGCTTGGTGGC (SEQ ID NO: 46) |
| YWHAE | GCTGATAGTTGAAGAAAGAAAGTTAATATTCATAGCT TTCTTTCTTCAACTGTCAGC (SEQ ID NO: 47) |

Six of the confirmed shRNA targets belong to Integrin/Rac signaling pathway (ITGAV, RAC1, ARHGAP1, RAPGEF1, CRKL, NCKAP1, CDC42), indicating that this pathway plays an indispensable role in maintenance of viability of senescent cells. These unexpected findings strongly suggest that inhibitors of this pathway may be exploited for inducing cell death in normal or tumor senescent cells.

In summary, the present disclosure is believed to provide for the first time a specific list targets for selective eradication of senescent cells. The disclosure is expected to lead to numerous practical medical and cosmetic applications and to provide a broadly applicable solution for treatment and prevention of cancer, aging and age-related diseases and conditions which currently have no one universal treatment approach.

Although the embodiments have been described in detail for the purposes of illustration, it is understood that such detail is solely for that purpose, and variations can be made therein by those skilled in the art without departing from the spirit and scope of the disclosure, embodiments of which are defined by the following sample claims.

I claim:

1. A method for selectively killing senescent cells in a mammal, wherein the mammal is suspected of having or is at risk for developing an age-related disease, comprising administering to the mammal at least one agent such that the expression of fibroblast growth factor 1 (FGF-1) is inhibited.

2. The method of claim 1, wherein the inhibition of the FGF-1 is achieved by RNAi-mediated downregulation of mRNA encoded by the FGF-1 gene.

3. The method of claim 2, wherein the agent is an shRNA, an siRNA, or an antisense oligonucleotide.

4. The method of claim 2, wherein the senescent cells are selected from irreversibly arrested cells present in connective tissue, epithelial tissue, and combinations of said senescent cells.

5. The method of claim 2, where senescent cells are irreversibly arrested melanocytes.

6. The method of claim 2, where senescent cells are irreversibly arrested tumor cells.

7. The method of claim 6, wherein the irreversibly arrested tumor cells are arrested subsequent to exposure to a chemotherapeutic agent or radiation.

8. The method of claim 7, where the senescent cells are eliminated from a tumor subsequent to treatment of the mammal by radiation or chemotherapy.

9. The method of claim 1, wherein the subject is in need of or is undergoing treatment for cancer.

10. The method of claim 9, wherein the cancer is selected from prostate cancer, melanoma, lung cancer, sarcoma, breast cancer, and colon cancer.

11. The method of claim 1, wherein the individual is in need of therapy for tissue impaired by accumulated senescent cells.

12. The method of claim 11, wherein the accumulated cells are present in a pigmented skin lesion.

13. The method of claim 1, wherein administering the agent improves the outcome of a cancer treatment of the mammal, wherein the cancer treatment is radiation or chemotherapy.

14. The method of claim 1, wherein the mammal is in need of treatment for a metastatic cancer, and wherein the administering the agent is such that dormant cancer cells in the mammal are killed.

15. The method of claim 1, wherein the mammal is a human.

16. The method of claim 1, where the mammal is a non-human mammal.

17. The method of claim 1, wherein lifespan of the mammal is increased subsequent to the administering of the agent.

18. The method of claim 1, wherein the age-related disease is Alzheimer's disease, Type II diabetes, macular degeneration, or a disease comprising chronic inflammation.

19. The method of claim 18, wherein the disease comprising chronic inflammation is arthritis.

* * * * *